United States Patent [19]
James et al.

[11] Patent Number: 6,046,136
[45] Date of Patent: Apr. 4, 2000

[54] HERBICIDAL HETEROCYCLIC N-OXIDES COMPOUNDS

[75] Inventors: Donald R. James, El Sobrante, Calif.; Christopher J. Mathews, Wokingham, United Kingdom

[73] Assignee: Zeneca Limited, United Kingdom

[21] Appl. No.: 08/881,709

[22] Filed: Jun. 24, 1997

[51] Int. Cl.[7] .......................... A01N 43/38; C07D 401/04
[52] U.S. Cl. .......................... 504/246; 504/252; 504/253; 546/275.7; 546/277.4; 546/268.4; 546/117; 546/118; 546/119; 546/120
[58] Field of Search .................. 546/275.7, 277.4, 546/268.4, 117, 118, 119, 120; 504/246, 253, 252

[56] References Cited

U.S. PATENT DOCUMENTS

| | | | |
|---|---|---|---|
| 3,960,542 | 6/1976 | Plant et al. | 546/290 |
| 5,300,478 | 4/1994 | Michaely et al. | 504/246 |
| 5,369,086 | 11/1994 | James et al. | 504/235 |
| 5,395,817 | 3/1995 | Pollos et al. | 504/252 |
| 5,428,003 | 6/1995 | Nielson et al. | 504/253 |
| 5,444,038 | 8/1995 | James et al. | 504/253 |
| 5,451,566 | 9/1995 | Mathews | 504/246 |

OTHER PUBLICATIONS

CA 122:125880, Ugryumov et al, 1995.
CA 95:216306, Soliman, 1981.

*Primary Examiner*—Jane Fan
*Attorney, Agent, or Firm*—David P. LeCroy

[57] ABSTRACT

This invention relates to novel optionally substituted heterocyclic N-oxide compounds of formula (I):

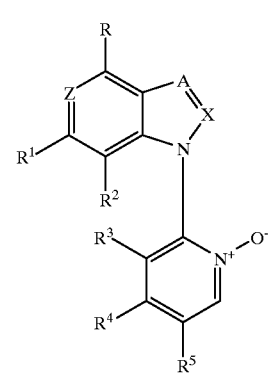

wherein: R, $R^1$, $R^2$, $R^3$, $R^4$, $R^5$, $R^6$, $R^7$, A, X, Z and m are defined herein. In other aspects, this invention relates to herbicidal compositions containing a optionally substituted heterocyclic N-oxide compound or derivative thereof and an agriculturally acceptable carrier and to a method of controlling undesirable vegetation by applying to an area where control is desired an herbicidally effective amount of an optionally substituted heterocyclic N-oxide compound or derivative thereof.

30 Claims, No Drawings

HERBICIDAL HETEROCYCLIC N-OXIDES COMPOUNDS

FIELD OF THE INVENTION

In one aspect, this invention relates to novel optionally substituted heterocyclic N-oxide compounds and derivatives thereof which exhibit unexpectedly desirable herbicidal activity. In other aspects, this invention relates to herbicidal compositions containing a optionally substituted heterocyclic N-oxide compound or derivative thereof and an agriculturally acceptable carrier and to a method of controlling undesirable vegetation by applying to an area where control is desired an herbicidally effective amount of an optionally substituted heterocyclic N-oxide compound or derivative thereof.

BACKGROUND OF THE INVENTION

The need for effective herbicides needs no special emphasis. The control of weeds and undesirable vegetation is of great economic importance since weed competition inhibits the production of foliage, fruit or seed of agricultural crops. The presence of weeds can reduce harvesting efficiency and the quality of the harvested crop. Weeds on non-cropped areas may cause a fire hazard, undesirable drifting of sand or snow, and/or irritation to persons with allergies. Thus, suppression of undesirable weed growth is very advantageous.

Accordingly, it is an object of this invention to provide effective novel herbicidal compounds, as well as to provide novel herbicidal compositions and novel methods of controlling weeds.

Various heterocyclic compounds useful as herbicides have been described in U.S. Pat. Nos. 5,451,566, 5,444,038 and 5,369,086 which are all incorporated herein by reference. For instance, U.S. Pat. No. 5,451,566 describes 1-aryl pyrrolopyridine compounds useful as herbicidal agents. In addition, U.S. Pat. No. 5,444,038 describes 1-arylindazole compounds which are useful as herbicides. Similarly, U.S. Pat. No. 5,369,086 describes 1-aryl-N-benzotriazoles. None of the aforementioned patents disclose a compound wherein the 1-aryl group is a pyridyl N-oxide which possesses herbicidal activity.

Surprisingly, the inventors have found that the heterocyclic pyridyl N-oxide compounds described herein below exhibit unexpectedly desirable herbicidal activity. The compounds have been found to be effective in both preemergent and postemergent application and on a variety of weed species.

SUMMARY OF THE INVENTION

In one aspect, this invention is directed to compounds of formula (I):

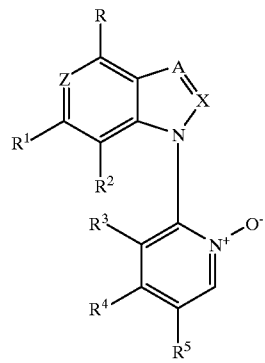

wherein:

R, $R^1$ and $R^7$ are independently hydrogen; halogen; cyano; $C_1$–$C_6$ alkyl; nitro; $C_1$–$C_6$ aloxy; $C_1$–$C_6$ haloalkyl; $C_1$–$C_6$ alkoxy-$C_1$–$C_6$-aklyl; formyl; $C_1$–$C_6$ alkylcarbonyl; $C_1$–$C_6$ alkylcarbonyloxy; $C_1$–$C_6$ alkoxycarbonyl-$C_1$–$C_6$ alkoxy; carboxy and its salts, esters and amides thereof, tetrahydrophthalimide; amino; substituted amino wherein the substituent(s) are selected from $C_1$–$C_6$ alkyl, $C_1$–$C_6$ alkoxy, hydroxy, formyl, $C_1$–$C_6$ alkylcarbonyl, $C_1$–$C_6$ alkoxycarbonyl, $C_1$–$C_6$ alkoxycarbonyl-$C_1$–$C_6$ alkylidenecarbonyl, hydroxycarbonyl-$C_1$–$C_6$ alkylidenecarbonyl, $C_1$–$C_6$ alkylsulfonyl, $C_1$–$C_6$ haloalkylsulfonyl, aminocarbonyl, (di) $C_1$–$C_6$ alkylaminocarbonyl, amino and (di) $C_1$–$C_6$ alkylamino; sulfamoyl; sulfonamdo wherein the N is substituted with $C_1$–$C_6$ alkyl; $QR^6$ wherein Q is —O— or $S(O)_m$— and $R^6$ is selected from hydrogen, $C_1$–$C_6$ alkyl, $C_1$–$C_6$ haloalkyl, cyano-$C_1$–$C_6$ alkyl, $C_1$–$C_6$ alkoxycarbonyl-$C_1$–$C_6$ alkyl, $C_2$–$C_4$ alkenyl, $C_3$–$C_6$ alkynyl, hydroxycarbonyl-$C_1$–$C_6$ alkyl and aminocarbonyl-$C_1$–$C_6$ alkyl wherein the nitrogen atom may be optionally substituted with $C_1$–$C_6$ alkyl, $C_1$–$C_6$ alkoxy, $C_1$–$C_6$ alkylsulfonyl, $C_1$–$C_6$ haloalkylsulfonyl, amino or (di) $C_1$–$C_6$ alkylamino;

$R^2$ is hydrogen, halogen, $C_1$–$C_6$ alkyl or nitro;

$R^3$ is hydrogen, nitro, halogen, cyano, $C_1$–$C_6$ alkyl-$S(O)_m$— or $C_1$–$C_6$ alkoxy;

$R^4$ is hydrogen or halogen;

$R^5$ is halogen, $C_1$–$C_6$ haloalkyl, cyano, or $C_1$–$C_6$ alkyl-$S(O)_m$—;

Z is N or C—$R^7$ wherein $R^7$ is defined as above; and

A and X are independently N, C—H or C-halogen; m is 0, 1 or 2; and agriculturally acceptable salts thereof.

In another aspect, this invention is directed to an herbicidal composition containing (A) a compound of formula (I)

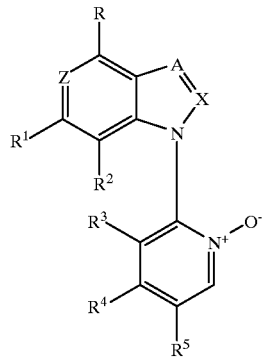
(I)

wherein R, $R^1$, $R^2$, $R^3$, $R^4$, $R^5$, $R^6$, $R^7$, A, X, Z and m have the same meanings as above, or an agriculturally acceptable salt thereof; and (B) a carrier therefor.

In still another aspect, this invention is directed to a method for controlling undesirable vegetation by applying to an area where such vegetation control is desired an herbicidally effective amount of a compound of formula (I):

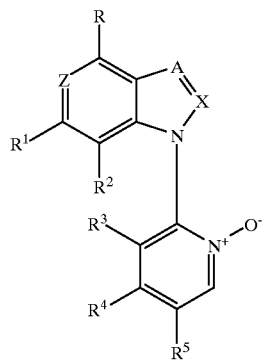
(I)

wherein R, $R^1$, $R^2$, $R^3$, $R^4$, $R^5$, $R^6$, $R^7$, A, X, Z and m have the same meanings as above, or an agriculturally acceptable salt thereof.

DETAILED DESCRIPTION OF THE INVENTION

The novel herbicidal compounds of this invention are of the formula (I):

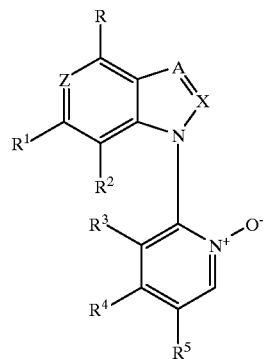
(I)

wherein R, $R^1$, $R^2$, $R^3$, $R^4$, $R^5$, $R^6$, $R^7$, A, X, Z and m have the same meanings as above; and agriculturally acceptable salts thereof.

In another aspect, this invention is directed to a herbicidal composition containing (A) a compound of formula (I)

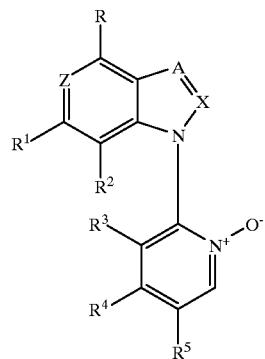
(I)

wherein R, $R^1$, $R^2$, $R^3$, $R^4$, $R^5$, $R^6$, $R^7$, A, X, Z and m have the same meanings as above; or an agriculturally acceptable salts thereof; and (B) a carrier thereof.

In still another aspect, this invention is directed to a method for controlling undesirable vegetation by applying to an area where such vegetation control is desired an herbicidally effective amount of a compound formula (I):

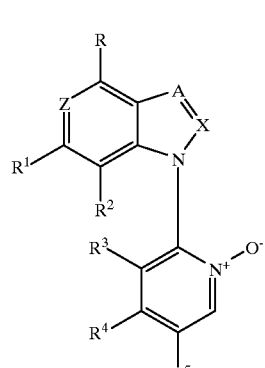
(I)

wherein R, $R^1$, $R^2$, $R^3$, $R^4$, $R^5$, $R^6$, $R^7$, A, X, Z and m have the same meanings as above; or an agriculturally acceptable salts thereof.

Preferably, R is hydrogen, halogen or nitro; $R^1$ is hydrogen, $C_1$–$C_6$ alkoxy or $C_1$–$C_6$ alkoxycarbonyl-$C_1$–$C_6$ alkoxy; $R^2$ is hydrogen; $R^3$ is hydrogen; $R^4$ is hydrogen; $R^5$ is $C_1$–$C_6$ haloalkyl; A is N or C—H; X is N or C—H and Z is N or $CR^7$ wherein $R^7$ is as defined above.

The expression "salts, amides and esters thereof" used above in relation to carboxy substitution includes, for example, salts formed from alkali metals (e.g., sodium, potassium and lithium), alkaline earth metals (e.g., calcium and magnesium), the ammonium ion and substituted ammonium ions wherein one, two, three or four of the hydrogen atoms have been replaced by optionally substituted $C_1$–$C_6$ hydrocarbyl moieties as defined above. Likewise, the carboxy substitution includes esters and amides which may be formed from the carboxy group and an optionally substituted $C_1$–$C_6$ hydrocarbyl moiety in the case of the ester, or an optionally substituted $C_1$–$C_6$ hydrocarbyl amine in the case of the amide.

In the above definitions, the term "halogen" includes fluoro, chloro, bromo and iodo groups. In polyhalogenated groups, the halogens may be the same or different.

As used herein, the term "tetrahydrophthalimide" means cis-1, 2, 3, 6-tetrahydrophthalimide and 3, 4, 5, 6-tetrahydrophthalimide.

The compounds of the present invention have been found to be active herbicides, possessing utility as pre-emergence and post-emergence herbicides. These compounds are useful against a wide range of plant species including broadleaf, grassy and perennial species. The compounds of this invention have also been found to be particularly effective in controlling undesirable vegetation typically found in rice crops.

The terms "herbicide" and "herbicidal" are used herein to denote the inhibitive control or modification of undesired plant growth. Inhibitive control and modification include all deviations from natural development, such as, total killing, growth retardation, defoliation, desiccation, regulation, stunting, tillering, stimulation, leaf burn and dwarfing. The term "herbicidally effective amount" is used to denote any amount which achieves such control or modification when applied to the undesired plants themselves or to the area in which these plants are growing. The term "plants" is intended to include germinated seeds, emerging seedlings and established vegetation, including both roots and aboveground portions.

The term "agriculturally acceptable salt" is easily determined by one of ordinary skill in the art and includes hydrohalide, acetic, sulfonic, phosphonic, inorganic and organic acid salts.

SYNTHESIS OF COMPOUNDS

In general, pyridyl N-oxide pyrrolopyridine compounds of formula I may be prepared by reacting a pyrrolopyridine of the formula:

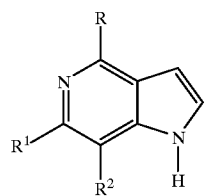

wherein R, $R^1$ and $R^2$ are as defined above, with a substituted N-oxide pyridine compound of the formula

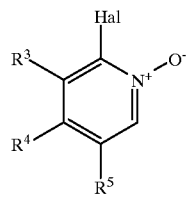

wherein hal is halogen; and $R^3$, $R^4$ and $R^5$ are as defined above; in the presence of a suitable base (such as a metal hydride or hydroxide) in a suitable solvent (such as dimethyl sulfoxide, or N,N-dimethylformamide).

The pyrrolopyridine starting materials may be prepared by methods described in the literature, such as by R. E. Willette, *Advances in Heterocyclic Chemistry*, 9, 27 (1968); or I. Mahadevan and M. Rasmussen, *J. Heterocyclic Chem.*, 29, 359 (1992).

The halogenated pyridine N-oxide starting materials are either commercially available or may be prepared by means well known to those of skill in the art.

The compositions of this invention may comprise a pyridyl N-oxide pyrrolopyridine compound of Formula (I) above and a suitable carrier, which carriers are well known to one of ordinary skill in the art.

The N-benzotriazole-pyridyl N oxide compounds of formula I may be prepared by the following procedure described herein below.

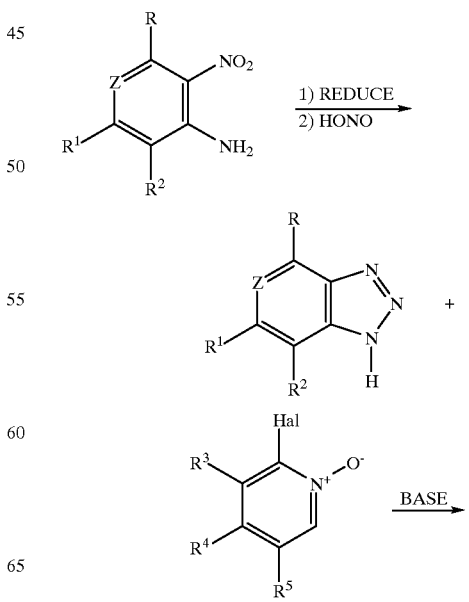

-continued

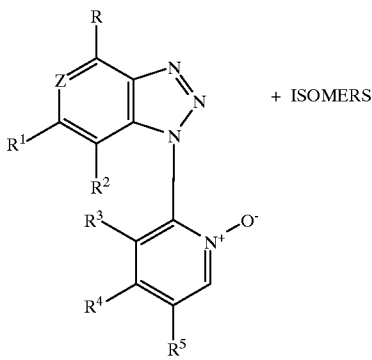

+ ISOMERS

Here, the ortho-Nitro anilines, prepared by nitration, of the corresponding anilide are readily reduced with iron in an alcohol/water mixture or by stannous chloride or other reducing metals salts in a similar manner. The resulting 1,2-phenylenediamines are readily cyclized to the final products with a source of nitrite, either inorganic metal nitrite salts in the presence of acid or organic nitrites such as isoamyl nitrite with-or-without an acid catalyst. The resulting benzotriazole are then arylated with the pyridine N-oxide as shown in the scheme above.

The indazole-N-oxide compounds of the formula

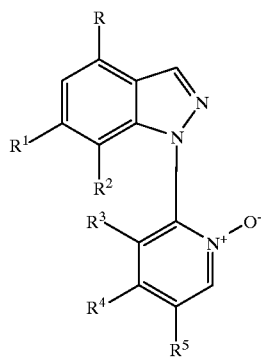

may be prepared using the following procedures:

Method A: The conversion of ortho-methylanilines to indazoles by the standard diazotization-cyclization route known in the art and described in *Organic Synthesis*, Collective Volume III, page 660.

In general, the aniline in glacial acetic acid is diazotized by the addition of aqueous sodium nitrite or an organic nitrite such as isoamyl nitrite in an organic solvent. The cyclization occurs slowly upon standing for several days or within several hours at the reflux temperature of the organic solvent.

Method B: Substituted cyclohexanones are allowed to react with an amide acetal at elevated temperatures to yield 2-(substituted) aminomethylene ketones. The ketone is condensed with hydrazine hydrate in alcohol solvent under reflux to yield tetrahydroindazoles. The saturated ring is then aromatized by heating in decalin containing palladium-on-carbon as a dehydration catalyst.

The unarylated indazoles can be further modified and substituted by a variety of known standard organic reactions, for example nitration, as found in standard textbooks such as *Advanced Organic Chemistry*, 4$^{th}$ edition by Jerry March, copyright 1992 by Wiley-Interscience.

The substituted indazole is then reacted with a pyridyl N-oxide to give a mixture of a target pyridyl N-oxide indazole and a minor isomer. The isomer can be removed by various techniques including recrystallization and column chromatography.

Nascent SH, OH, and NH$_2$ groups on the indazole ring can be alkylated, acylated and sulfonated or otherwise allowed to react with aryl isocyanates, alkyl isocyanates, acyl isocyanates or sulfonyl isocyanates to give desired products.

The compounds of the present invention are useful as herbicides and can be applied in a variety of ways known to those skilled in the art, at various concentrations. The compounds are useful in controlling the growth of undesirable vegetation by pre-emergent or post-emergent application to the locus where control is desired. The compositions of this invention comprise a compound of formula (I) above and a suitable carrier, which carriers are well known to one of ordinary skill in the art.

In practice, the compounds are applied as formulations containing the various adjuvants and carriers known to or used in the industry for facilitating dispersion. The choice of formulation and mode of application for any given compound may affect its activity, and selection will be made accordingly. The compounds of the invention may thus be formulated as wettable powders, as emulsifiable concentrates, as powders or dusts, as flowables, as solutions, suspensions or emulsions, or in controlled-release forms such as microcapsules. These formulations may contain as little as about 0.5% to as much as about 95% or more by weight of active ingredient. The optimum amount for any given compound will depend upon the nature of plants to be controlled. The rate of application will generally vary from about 0.01 to about 11.5 kilograms per hectare, preferably from about 0.02 to about 4.5 kilograms per hectare.

Wettable powders are in the form of finely divided particles which disperse readily in water or other liquid carriers. The particles contain the active ingredient retained in a solid matrix. Typical solid matrices include fuller's earth, kaolin clays, silicas and other readily wettable organic or inorganic solids. Wettable powders normally contain about 5% to about 95% of the active ingredient plus a small amount of wetting, dispersing, or emulsifying agent.

Emulsifiable concentrates are homogeneous liquid compositions dispersible in water or other liquid, and may consist entirely of the active compound with a liquid or solid emulsifying agent, or may also contain a liquid carrier, such as xylene, heavy aromatic naphthas, isophorone and other nonvolatile organic solvents. In use, these concentrates are dispersed in water or other liquid and normally applied as a spray to the area to be treated. The amount of active ingredient may range from about 0.5% to about 95% of the concentrate.

Dusts are free-flowing admixtures of the active ingredient with finely divided solids such as talc, clays, flours and other organic and inorganic solids which act as dispersants and carriers.

Microcapsules are typically droplets or solutions of the active material enclosed in an inert porous shell which allows escape of the enclosed material to the surrounds at controlled rates. Encapsulated droplets are typically about 1 to 50 microns in diameter. The enclosed material typically constitutes about 50 to 95% of the weight of the capsule, and may include solvent in addition to the active compound. Shell of membrane materials include natural and synthetic rubbers, cellulosic materials, styrene-butadiene copolymers, polyacrylonitriles, polyacrylates, polyesters, polyamides, polyureas, polyurethanes and starch xanthates.

Other useful formulations for herbicidal applications include simple solutions of the active ingredient in a solvent in which it is completely soluble at the desired concentration, such as water, acetone, alkylated naphthalenes, xylene and other organic solvents. Pressurized sprayers, wherein the active ingredient is dispersed in finely-divided form as a result of vaporization of a low boiling dispersant solvent carrier may also be used.

Many of these formulations include wetting, dispersing or emulsifying agents. Examples are alkyl and alkylaryl sulfonates and sulfates and their salts; polyhydric alcohols; polyethoxylated alcohols; esters and fatty amines. These agents when used normally comprise from 0.1% to 15% by weight of the formulation.

Each of the above formulations can be prepared as a package containing the herbicide together with other ingredients of the formulation (diluents, emulsifiers, surfactants, etc.). The formulations can also be prepared by a tank mix method, in which the ingredients are obtained separately and combined at the grower site.

The compounds of the present invention are also useful when combined with other herbicides and/or defoliants, desiccants, growth inhibitors, and the like. These other materials can comprise from about 5% to about 95% of the active ingredients in the formulations. These combinations frequently provide a higher level of effectiveness in controlling weeds and often provide results unattainable with separate formulations of the individual herbicides.

Examples of other herbicides, defoliants, desiccants and plant growth inhibitors with which the compounds of this invention can be combined are:

A. Benzo-2,1,3-thiadiazin-4-one-2,2-dioxides such as bentazone;

B. hormone herbicides, particularly the phenoxyalkanoic acids such as MCPA, MCPA-thioethyl, dichlorprop, 2,4,5-T, MCPB, 2,4-D, 2,4-DB, mecoprop, trichlopyr, fluroxypyr, clopyralid, and their derivatives (e.g. salts, esters and amides);

C. pyrazole derivatives such as pyrazoxyfen, pyrazolate and benzofenap;

D. dinitrophenols and their derivatives (e.g. acetates such as DNOC, dinoterb, dinoseb and its ester, dinoseb acetate;

E. dinitroaniline herbicides such as dinitramine, trifluralin, ethalfluralin, pendimethalin; and oryzalin;

F. arylurea herbicides such as diuron, flumeturon, metoxuron, neburon, isoproturon, chlorotoluron, chloroxuron, linuron, monolinuron, chlorobromuron, daimuron, and methabenzthiazuron;

G. phenylcarbamoyloxyphenylcarbamates such as phenmedipham and desmedipham;

H. 2-phenylpyridazin-3-ones such as chloridazon, and norflurazon;

I. uracil herbicides such as lenacil, bromacil and termacil;

J. triazine herbicides such as atrazine, simazine, aziprotryne, cyanazine, prometryn, dimethametryn, simetryne, and terbutryn;

K. phosphorothioate herbicides such as piperophos, bensulide, and butamifos;

L. thiolcarbamate herbicides such as cycloate, vemolate, molinate, thiobencarb, butylate*, EPTC*, triallate, diallate, ethyl esprocarb, tiocarbazil, pyridate, and dimepiperate;

* These compounds are preferably employed in combination with a safener such as 2,2-dichloro-N,N-di-2-propenylacetamide (dichlormid).

M. 1,2,4-triazin-5-one herbicides such as metamitron and metribuzin;

N. benzoic acid herbicides such as 2,3,6-TBA, dicamba and chloramben;

O. anilide herbicides such as pretilachlor, butachlor, the corresponding alachlor, the corresponding compound propachlor, propanil, metazachlor, metolachlor, acetochlor, and dimethachlor;

P. dihalobenzonitrile herbicides such as dichlobenil, bromoxynil and ioxynil;

Q. haloalkanoic herbicides such as dalapon, TCA and salts thereof;

R. diphenylether herbicides such as lactofen, flurogly-cofen or salts or esters thereof, nitrofen, bifenox, acifluorfen and salts and esters thereof, oxyfluorfen and fomesafen; chlornitrofen and chlomethoxyfen;

S. phenoxyphenoxypropionate herbicides such as diclofop and esters thereof such the methyl ester, fluazifop and esters thereof, haloxyfop and esters thereof, quizalofop and esters thereof and fenoxaprop and esters thereof such as the ethyl ester;

T. triketone and cyclohexanedione herbicides such as alloxydim and salts thereof, sethoxydim, cycloxydim, sulcotrione, tralkoxydim, and clethodim;

U. sulfonyl urea herbicides such as chlorosulfuron, sulfometuron, metsulfuron and esters thereof; benzsulfuron and esters thereof such as the ester thereof methyl, DPX-M6313, chlorimuron and esters such as the ethyl ester thereof, pirimisulfuron and esters such as the methyl ester thereof, DPX-LS300 and pyrazosulfuron;

V. imidazolidinone herbicides such as imazaquin, imazamethabenz, imazapyr and isopropylammonium salts thereof, imazathapyr;

W. arylanilide herbicides such as flamprop and esters thereof, benzoylprop-ethyl, diflufenican;

X. amino acid herbicides such as glyphosate and gluyfosinate and their salts and esters, sulphosate, and bilanafos;

Y. organoarsenical herbicides such as MSMA;

Z. herbicidal amide derivative such as napropamide, propyzamide, carbetamide, tebutam, bromobutide, isoxaben, naproanilide, diphenamid, and naptalam;

AA. 4-benzoylisoxazole and 2-cyano-1,3-dione herbicides.

BB. miscellaneous herbicides including ethofumesate, cinmethylin, difenzoquat and salts thereof such as the methyl sulfate salt, clomazone, oxadiazon, bromofenoxim, barban, tridiphane, flurochloridone, quinchlorac and mefanacet; and CC. contact herbicides, examples of which include bipyridylium herbicides such as those in which the active entity is paraquat and those in which the active entity is diquat.

These formulations can be applied to the areas where control is desired by conventional methods. Dust and liquid compositions, for example, can be applied by the use of powderdusters, boom and hand sprayers and spray dusters. The formulations can also be applied from airplanes as a dust or a spray or by rope wick applications.

The following are examples of typical formulations:

5% dust: 5 parts active compound 95 parts talc

2% dust: 2 parts active compound 1 part highly dispersed silicic acid 97 parts talc These dusts are formed by mixing the components then grinding the mixture to the desired particle size.

Wettable powders:
- 70%: 70 parts active compound 5 parts sodium dibutyl-naphthylsulfonate 3 parts naphthalenesulfonic acid/phenolsulfonic acid/phenol-sulfonic acid/formaldehyde condensate (3:2:1) 10 parts kaolin 12 parts Champagne chalk
- 40%: 40 parts active compound 5 parts sodium lignin sulfonate 1 part sodium dibutylnaphthalene sulfonic acid 54 parts silicic acid
- 25% 25 parts active compound 4.5 parts calcium lignin sulfate 1.9 parts Champagne chalk/-hydroxyethyl cellulose (1:1) 8.3 parts sodium aluminum silicate 16.5 parts kieselguhr 46 parts kaolin
- 10% 10 parts active compound 3 parts of a mixture of sodium salts of saturated fatty alcohol sulfates 5 parts naphthalenesulfonic acid/formaldehyde condensate 82 parts kaolin These wettable powders are prepared by intimately mixing the active compounds with the additives in suitable mixers, and grinding the resulting mixture in mills or rollers.
Emulsifiable concentrate:
- 25% 25 parts active substance 2.5 parts epoxidized vegetable oil 10 parts of an alkylarylsulfonate/fatty alcohol polyglycol ether mixture 57.5 parts xylene The amount of the present compositions which constitute a herbicidally effective amount depends upon the nature of the seeds or plants to be controlled. The rate of application of active ingredients varies from about 0.01 to about 28 kilograms per hectare, preferably about 0.02 to about 11 kilograms per hectare with the actual amount depending on the overall costs and the desired results. It will be readily apparent to one skilled in the art that compositions exhibiting lower herbicidal activity will require a higher dosage than more active compounds for the same degree of control.

EXAMPLES

The following examples are intended to further illustrate the present invention and are not intended to limit the scope of this invention in any manner whatsoever.

Example 1

Preparation of Compound 1

4-Chloro-1-(5-trifluoromethyl-2-pyridyl)-[3,2-c]-pyrrolopyridine N-Oxide

Sodium hydride (0.09 g, 3.6 mmol, [0.14 g of a 60% dispersion in oil]) was added to an ice-bath cooled solution of 4-chloro-1-H-pyrrolo[3,2-c]pyridine (0.55 g, 3.6 mmol) in N,N-dimethylformamide (10 ml) and the mixture stirred for a few minutes. 2-Chloro-5-trifluoromethylpyridine N-oxide (0.71 g, 3.6 mmol) was added and the mixture stirred for 4 hours, warming slowly to room temperature.

The mixture was poured into water, neutralized with acetic acid and extracted with chloroform. The organic extract was dried (MgSO$_4$), filtered and the filtrate evaporated in vacuo. The residue was further purified by flash column chromatography (3% methanol in dichloromethane) to give an orange-brown solid. Sequential trituration with hexane and diethyl ether gave the desired product (0.35 g) as a colorless solid. M.P.>190° C. dec.

Example 2

Preparation of Compound 2

4-Chloro-1-(5-trifluoromethyl-2-pyridyl) indazole N-Oxide

A. Preparation of 2-Chloro-5-Trifluoromethylpyridine N-Oxide

A solution of the 2-chloro-5-trifluoromethylpyridine (1.8 g, 0.01 mol) in methylene chloride (20 ml) was mixed with trifluoroacetic anhydride (15 g, 0.071 mol). The stirred solution was subjected to the dropwise addition of 30% aqueous hydrogen peroxide (1.4 g, 0.012 mol) over the course of 15 minutes. A mild exotherm ensued and the mixture was allowed to stir at ambient temperature for 1 hour. The solution was poured onto ice and extracted with 3×50 ml of ethyl acetate; the combined organic layers then were passed through a 1 inch pad of silica gel in a sintered glass funnel under suction. The eluate was evaporated and the residue was chromatographed on silica gel, eluting first with methylene chloride to remove unreacted pyridine and then with ethyl acetate to remove the product N-oxide weighing 1.8 g (90%) as an orange oil.

B. Preparation of 4-Chloro-1-(5-trifluoromethyl-2-pyridyl) indazole N-Oxide

A mixture of 2-chloro-5-trifluoromethylpyridine N-Oxide (1.8 g, 0.009 mol), 4-chloroindazole (1.1 g, 0.007 mol), anhydrous potassium carbonate (1.5 g, 0.0105 mol) and dimethylformamide (20 ml) was stirred and warmed to 70° C. Within 1 hour the reaction was complete based on thin-layer chromatographic analysis. The solution was poured into brine (300 ml) and the precipitate was collected by suction filtration and was washed with water until the filtrate was clear. The brick-red solid was air dried to yield 1.6 g (73%) of the desired product, m.p. 154° C. (dec).

TABLE I

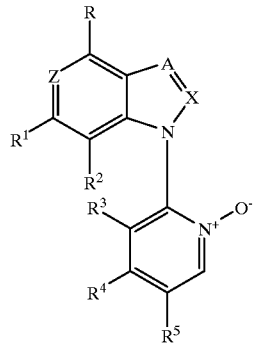

| Comp No. | R | R¹ | R² | R³ | R⁴ | R⁵ | X | A | Z |
|---|---|---|---|---|---|---|---|---|---|
| 1 | Cl | H | H | H | H | CF₃ | CH | CH | N |
| 2 | Cl | H | H | H | H | CF₃ | N | CH | CH |
| 3 | H | OCH₃ | H | H | H | CF₃ | N | CH | C—NO₂ |
| 4 | H | CH₃CH₂O-C(=O)-CH(CH₃)-O- | H | H | H | CF₃ | N | CH | CH |
| 5 | CN | H | H | H | H | CF₃ | N | CH | N |
| 6 | Cl | H | H | H | H | CF₃ | N | CH | C—CH₃ |
| 7 | F | H | H | H | H | CF₃ | N | CH | CH |
| 8 | H | H | H | H | H | CF₃ | N | CH | C—F |
| 9 | H | H | H | H | H | CF₃ | N | CH | C—CH₃ |
| 10 | H | H | H | H | H | CF₃ | N | CH | C—Cl |
| 11 | CH₃ | H | H | H | H | CF₃ | N | CH | CH |
| 12 | H | H | H | H | H | CF₃ | N | CH | C—CN |
| 13 | H | (tetrahydrophthalimido group) | H | H | H | CF₃ | N | CH | CH |

HERBICIDAL SCREENING TESTS

The compounds listed in the foregoing table were tested for herbicidal activity by various methods and at various rates of application. The results of some of these tests are given below. Results obtained in herbicidal screening are affected by a number of factors including: the amount of sunlight, soil type, soil pH, temperature, humidity, depth of planting, plant growth stage, application rate as well as many other factors. All testing procedures are administered with the least amount of variability possible. State of the art equipment and techniques are employed to enable the screening process to remain consistent and reliable.

PRE-EMERGENCE HERBICIDAL SCREENING TEST

On the day preceding treatment, seeds of several different weed species were planted in sandy loam soil containing only trace organic matter. Propagules were sown in individual rows using one species per row across the width of an aluminum flat. Seeding depths ranged from 1.0 to 1.5 cm and plant densities ranged from 3 to 25 plants per row depending on individual plant species.

The grass weeds planted (Table II) were broadleaf signalgrass (*Brachiaria platyphylla*) "BRAPP"; large crabgrass (*Digitaria sanguinalis*) "DIGSA"; barnyardgrass (*Echinochloa crusgalli*) "ECHCG"; rigid ryegrass (*Lolium rigidum*) "LOLRI"; fall panicum (*Panicum dichotomiflorum*) "PANDI"; giant foxtail (*Setari faberi*) "SETFA"; green foxtail (*Setaria viridis*) "SETVI"; blackgrass (*Alopecurus myosuroides*) "ALOMY"; wild oat (*Avena fatua*) "AVEFA" and Johnsongrass (*Sorghum halepense*) "SORHA".

The broadleaf weeds planted (Table III) were velvefleaf (*Abutilon theophrasti*) "ABUTH"; redroot pigweed (*Amaranthus retroflexus*) "AMARE"; common lambsquarters (*Chenopodium album*) "CHEAL"; ivyleaf morningglory (*Ipomoea hederacea*) "IPOHE"; common purslane (*Portulaca oleracea*) "POROL"; common cockleburr (*Xanthium strumarium*) "XANST"; and catchweed bedstraw (*Galium aparine*) "GALAP". Additionally, yellow nutsedge (*Cyperus esculentus*) "CYPES" nutlets were also sown.

Solutions of the test compounds were prepared by weighing out an appropriate amount of the test compound to provide an application rate of 0.25 kilograms per hectare (kg/ha), then dissolving the compound in a 50:50 mixture of deionized water and acetone containing 0.5% v/v Tween 20® (polyoxyethylene sorbitan monolaurate emulsifier) as a surfactant. Additional solvents, not exceeding 15% of spray volume, were used if needed to dissolve the compound.

The soil surface was sprayed inside an enclosed linear spray table with the nozzle set above the soil line. The spray table was calibrated to deliver 400 L/ha with the application rate being 0.25 kg/ha. After treatment, the flats were placed into a greenhouse and watered as needed. The greenhouse environmental systems provided the plants with natural and artificial lighting to attain 14 hours of light per day. Day and night temperatures were maintained at 29° and 21° C., respectively.

The degree of weed control was evaluated and recorded 17–21 days after treatment as a percentage of weed control as compared to the growth of the same species of the same age in an untreated control flat. Percent control is the total injury to the plants due to all factors including: inhibited emergence, stunting, malformation, chlorosis and other types of plant injury. The results of the pre-emergence screening tests are shown in Tables II and III below. The control ratings range from 0 to 100 percent, where 0 represents no effect with growth equal to the untreated control and where 100 represents complete kill. The symbol "--" indicates that no test was performed at the 0.25 kg/ha level of application.

TABLE II

PRE-EMERGENCE SCREENING

| COMP NO. | BRAPP | DIGSA | ECHCG | LOLRI | PANDI | SETFA | SETVI | ALOMY | AVEF | SORHA |
|---|---|---|---|---|---|---|---|---|---|---|
| 1 | 100 | 100 | 100 | 100 | 100 | 100 | 100 | 100 | 100 | 100 |
| 2 | 100 | — | 100 | 99 | 100 | 99 | 100 | 99 | 98 | 99 |
| 3 | 0 | — | 3 | 0 | 85 | 99 | 99 | 10 | 25 | 60 |
| 5 | 0 | — | 0 | 0 | 0 | 0 | 25 | 0 | — | 10 |
| 6 | 99 | — | 88 | 60 | 100 | 100 | 100 | 90 | — | 60 |
| 7 | 0 | — | 0 | 0 | 100 | 0 | 70 | 10 | — | 10 |
| 8 | 0 | — | 0 | 0 | 0 | 0 | 5 | 0 | — | 0 |
| 11 | 0 | — | 0 | 0 | 0 | 0 | 0 | 0 | — | 0 |

TABLE III

PRE-EMERGENCE SCREENING

| COMP. NO. | ABUTH | AMARE | CHEAL | IPOHE | POROL | XANST | GALAP | CYPES |
|---|---|---|---|---|---|---|---|---|
| 1 | 100 | 100 | 100 | 15 | 100 | 0 | 100 | 82 |
| 2 | 100 | 100 | 98 | 25 | 100 | 5 | 99 | 20 |
| 3 | 100 | 65 | 100 | 0 | 100 | — | 30 | 0 |
| 5 | 0 | 0 | 30 | 0 | 100 | 0 | 35 | 0 |
| 6 | 100 | 100 | 100 | 12 | 100 | 0 | 99 | 0 |
| 7 | 0 | 0 | 10 | 60 | 97 | 0 | 10 | 0 |
| 8 | 0 | 0 | 0 | 0 | 0 | 0 | 0 | 0 |
| 11 | 0 | 0 | 0 | 0 | 0 | 0 | 0 | 0 |

Using similar conditions as above, the following weed species were used for compounds 9, 10, 12 and 13 in a pre-emergence screening test. The grass weeds planted were green foxtail (*Setaria viridis*) ("SETVI"), wild oat (*Avena fatua*) ("AVEFA"), barnyardgrass (*Echinochloa crusgalli*) ("ECHCG") blackgrass (*Alopecurus myosuroides*) ("ALOMY"). Broadleaf weeds utilized were wild mustard (*Sinapis arvensis*) ("SINAR"), velvetleaf (*Abutilon theophrasti*) ("ABUTH") and morningglory (*Ipomoea spp.*) ("IPOSS"). Additionally, yellow nutsedge (*Cyperus esculentus*) ("CYPES"), nutlets were sown (Table IV).

TABLE IV

PRE-EMERGENCE SCREENING

| COMP. NO. | ALOMY | AVEFA | ECHCG | SETVI | ABUTH | IPOSS | SINAR | CYPES |
|---|---|---|---|---|---|---|---|---|
| 9 | 5 | 0 | 5 | 10 | 0 | 0 | 0 | 0 |
| 10 | 10 | 0 | 10 | 70 | 0 | 0 | 0 | 0 |
| 12 | 10 | 0 | 0 | 10 | 0 | 0 | 0 | 0 |
| 13 | 0 | 0 | 0 | 10 | 0 | 0 | 0 | 0 |

POST-EMERGENCE HERBICIDAL SCREENING TEST

The soil was prepared with the same methodology described for the pre-emergence test. The following species were used.

The grass weeds planted were "BRAPP"; "ECHCG"; "LOLRI"; "PANDI"; "SETFA"; "SETVI"; "ALOMY"; "AVEFA" and "SORHA".

The broadleaf weeds planted were "ABUTH"; "AMARE"; "CHEAL"; "IPOHE"; "POROL"; "XANST"; "GALAP" and scentless chamomile (*Matricaria perforata*) "MATIN". Additionally, "CYPES" nutlets were also sown.

Post-emergence flats were placed in the greenhouse under the same environmental conditions as described for the pre-emergence flats and watered as needed. Plants were grown for 10 to 12 days (or to the appropriate growth stage) prior to compound application. Grasses were sprayed at a 3 to 4 leaf stage and broadleaves at a 1 to 2 leaf stage. Yellow nutsedge was 5 to 7 cm tall at application.

Plants were sprayed 30.5 cm (12 inches) above the foliage with the same spray solution as prepared for the pre-emergence test. The application rate was 0.25 kg/ha. Treated plants were then returned to a greenhouse and watered daily without wetting the foliage. The degree of weed control was evaluated 17–21 days after application and recorded as percentage of control as compared to the growth of the same species in an untreated control flat of the same age. The percent control scale (0–100%) used to evaluate the pre-emergence treatment was also applied to the post-emergence treatment. The post-emergence screening test results are shown in Table V (grass weeds) and Table VI (broadleaf weeds) below.

TABLE V

POST EMERGENCE SCREENING

| COMP. NO. | BRAPP | ECHCG | LOLRI | PANDI | SETFA | SETVI | ALOMY | AVEFA | SORHA |
|---|---|---|---|---|---|---|---|---|---|
| 1 | 25 | 20 | 70 | 25 | 20 | 80 | 90 | 98 | 75 |
| 2 | 30 | 15 | 30 | 60 | 65 | 45 | 60 | 70 | 45 |
| 3 | 10 | 5 | 0 | 25 | 10 | 35 | 40 | 10 | 15 |
| 5 | 0 | 0 | 0 | 0 | 0 | 0 | 0 | 0 | 0 |
| 6 | 10 | 10 | 0 | 5 | 10 | 50 | 45 | 40 | 15 |
| 7 | 10 | 10 | 0 | 5 | 5 | 10 | 0 | 0 | 30 |
| 8 | 0 | 0 | 0 | 0 | 0 | 5 | 0 | 0 | 10 |
| 11 | 0 | 0 | 0 | 20 | 0 | 0 | 0 | 0 | 0 |

TABLE VI

POST-EMERGENCE SCREENING

| COMP. NO. | ABUTH | AMARE | CHEAL | IPOHE | POROL | XANST | GALAP | MATIN | CYPES |
|---|---|---|---|---|---|---|---|---|---|
| 1 | 100 | 100 | 100 | 100 | 100 | 100 | 100 | 100 | 100 |
| 2 | 40 | 40 | 80 | 80 | 100 | 40 | 98 | 55 | 15 |
| 3 | 60 | 100 | 90 | 100 | 100 | 10 | 70 | 10 | 20 |
| 5 | 0 | 60 | 65 | 5 | 20 | 3 | 50 | 0 | 0 |
| 6 | 40 | 100 | 85 | 90 | 80 | 25 | 70 | 5 | 0 |
| 7 | 0 | 50 | 35 | 50 | 25 | 5 | 25 | 10 | 0 |
| 8 | 0 | 0 | 0 | 15 | 40 | 0 | 0 | 0 | 0 |
| 11 | 0 | 70 | 24 | 5 | 10 | 0 | 0 | 0 | 0 |

Using similar conditions as above, the following weed species were used for compounds 9, 10, 12 and 13 in a post-emergence screening test.

The grass weeds planted were green foxtail (*Setaria viridis*) ("SETVI"), wild oat (*Avena fatua*) ("AVEFA"), barnyardgrass (*Echinochloa crusgalli*) ("ECHCG"), blackgrass (*Alope curus myosuroides*) ("ALOMY"). Broadleaf weeds utilized were wild mustard (*Sinapis arvensis*) ("SINAR"), velvetleaf (*Abutilon theophrasti*) ("ABUTH") and morningglory (*Ipomoea spp.*) ("IPOSS"). Additionally, yellow nutsedge (*Cyperus esculentus*) ("CYPES"), nutlets were sown (Table VII).

TABLE VII

POST-EMERGENCE SCREENING

| COMP. NO. | ALOMY | AVEFA | ECHCG | SETVI | ABUTH | POSS | SINAR | CYPES |
|---|---|---|---|---|---|---|---|---|
| 9 | 25 | 0 | 10 | 5 | 5 | 20 | 5 | 0 |
| 10 | 0 | 0 | 0 | 5 | 0 | 15 | 0 | 0 |
| 12 | 0 | 0 | 0 | 0 | 0 | 0 | 0 | 0 |
| 13 | 20 | 5 | 5 | 35 | 60 | 80 | 10 | 5 |

Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims.

What is claimed is:
1. A compound of formula (I),

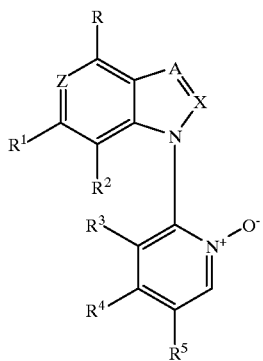

(I)

wherein:
R, $R^1$ and $R^7$ are independently hydrogen; halogen; cyano; $C_1$–$C_6$ alkyl; nitro; $C_1$–$C_6$ alkoxy; $C_1$–$C_6$ haloalkyl; $C_1$–$C_6$ alkoxy-$C_1$–$C_6$-alkyl; formyl; $C_1$–$C_6$ alkylcarbonyl; $C_1$–$C_6$ alkylcarbonyloxy; $C_1$–$C_6$ alkoxycarbonyl-$C_1$–$C_6$ alkoxy; carboxy and its salts, esters and amides thereof; tetrahydrophthalimide; amino; substituted amino wherein the substituent(s) are selected from $C_1$–$C_6$ alkyl, $C_1$–$C_6$ alkoxy, hydroxy, formyl, $C_1$–$C_6$ alkylcarbonyl, $C_1$–$C_6$ alkoxycarbonyl, $C_1$–$C_6$ alkoxycarbonyl-$C_1$–$C_6$ alkylidenecarbonyl, hydroxycarbonyl-$C_1$–$C_6$ alkylidenecarbonyl, $C_1$–$C_6$ alkylsulfonyl, $C_1$–$C_6$ haloalkylsulfonyl, aminocarbonyl, (di) $C_1$–$C_6$ alkylaminocarbonyl, amino and (di) $C_1$–$C_6$ alkylamino; sulfamoyl; sulfonamido wherein the N is substituted with $C_1$–$C_6$ alkyl; $QR^6$ wherein Q is —O— or $S(O)_m$— and $R^6$ is selected from hydrogen, $C_1$–$C_6$ alkyl, $C_1$–$C_6$ haloalkyl, cyano-$C_1$–$C_6$ alkyl, $C_1$–$C_6$ alkoxycarbonyl-$C_1$–$C_6$ alkyl, $C_2$–$C_4$ alkenyl, $C_3$–$C_6$ alkynyl, hydroxycarbonyl-$C_1$–$C_6$ alkyl and aminocarbonyl-$C_1$–$C_6$ alkyl wherein the nitrogen atom may be optionally substituted with $C_1$–$C_6$ alkyl, $C_1$–$C_6$ alkoxy, $C_1$–$C_6$ alkylsulfonyl, $C_1$–$C_6$ haloalkylsulfonyl, amino or (di) $C_1$–$C_6$ alkylamino;

$R^2$ is hydrogen, halogen, $C_1$–$C_6$ alkyl or nitro;

$R^3$ is hydrogen, nitro, halogen, cyano, $C_1$–$C_6$ alkyl-$S(O)_m$— or $C_1$–$C_6$ alkoxy;

$R^4$ is hydrogen or halogen;

$R^5$ is halogen, $C_1$–$C_6$ haloalkyl, cyano, or $C_1$–$C_6$ alkyl-$S(O)_m$—;

Z is N or C—$R^7$ wherein $R^7$ is defined as above; and

A and X are independently N, C—H or C-halogen; m is 0, 1 or 2; or an agriculturally acceptable salt thereof.

2. A compound according to claim 1 wherein, Z is N; and A and X are C—H or an agriculturally acceptable salt thereof.

3. A compound according to claim 1 wherein R is halogen; cyano; $C_1$–$C_6$ alkyl; $C_1$–$C_6$ haloalkyl; $C_1$–$C_6$ alkoxy-$C_1$–$C_6$-alkyl; formyl; $C_1$–$C_6$ alkylcarbonyl; $C_1$–$C_6$ alkylcarbonyloxy; $C_1$–$C_6$ alkoxycarbonyl-$C_1$–$C_6$ alkoxy; carboxy and its salts, esters and amides thereof; tetrahydrophthalimide; amino; substituted amino wherein the substituent(s) are selected from $C_1$–$C_6$ alkyl, $C_1$–$C_6$ alkoxy, hydroxy, formyl, $C_1$–$C_6$ alkylcarbonyl, $C_1$–$C_6$ alkoxycarbonyl, $C_1$–$C_6$ alkoxycarbonyl-$C_1$–$C_6$ alkylidenecarbonyl, hydroxycarbonyl-$C_1$–$C_6$ alkylidenecarbonyl, $C_1$–$C_6$ alkylsulfonyl, $C_1$–$C_6$ haloalkylsulfonyl, aminocarbonyl, (di) $C_1$–$C_6$ alkylaminocarbonyl, amino and (di) $C_1$–$C_6$ alkylamino; sulfamoyl; sulfonamido wherein the N is substituted with $C_1$–$C_6$ alkyl; $QR^6$ wherein Q is —O— or $S(O)_m$— and $R^6$ is selected from hydrogen, $C_1$–$C_6$ alkyl, $C_1$–$C_6$ haloalkyl, cyano-$C_1$–$C_6$ alkyl, $C_1$–$C_6$ alkoxycarbonyl-$C_1$–$C_6$ alkyl, $C_2$–$C_4$ alkenyl, $C_3$–$C_6$ alkynyl, hydroxycarbonyl-$C_1$–$C_6$ alkyl and aminocarbonyl-$C_1$–$C_6$ alkyl wherein the nitrogen atom may be optionally substituted with $C_1$–$C_6$ alkyl, $C_1$–$C_6$ alkoxy, $C_1$–$C_6$ alkylsulfonyl, $C_1$–$C_6$ haloalkylsulfonyl, amino or (di) $C_1$–$C_6$ alkylamino; Z is N; and A and X are CH; or an agriculturally acceptable salt thereof.

4. A compound according to claim 3 wherein $R^3$ is chloro or fluoro; $R^4$ is hydrogen and $R^5$ is trifluoromethyl.

5. A compound according to claim 3 wherein R is chloro; $R^1$ is hydrogen; $R^2$ is hydrogen; $R^3$ is hydrogen; $R^4$ is hydrogen and $R^5$ is trifluoromethyl.

6. A compound according to claim 1 wherein Z is C—$R^7$ wherein $R^7$ is hydrogen; halogen; cyano; $C_1$–$C_6$ alkyl; nitro; $C_1$–$C_6$ alkoxy; $C_1$–$C_6$ haloalkyl; $C_1$–$C_6$ alkoxy-$C_1$–$C_6$-alkyl; formyl; $C_1$–$C_6$ alkylcarbonyl; $C_1$–$C_6$ alkylcarbonyloxy; $C_1$–$C_6$ alkoxycarbonyl-$C_1$–$C_6$ alkoxy; carboxy and its salts, esters and amides thereof; tetrahydrophthalimide; amino; substituted amino wherein the substituent(s) are selected from $C_1$–$C_6$ alkyl, $C_1$–$C_6$ alkoxy, hydroxy, formyl, $C_1$–$C_6$ alkylcarbonyl, $C_1$–$C_6$ alkoxycarbonyl, $C_1$–$C_6$ alkoxycarbonyl-$C_1$–$C_6$ alkylidenecarbonyl, hydroxycarbonyl-$C_1$–$C_6$ alkylidenecarbonyl, $C_1$–$C_6$ alkylsulfonyl, $C_1$–$C_6$ haloalkylsulfonyl, aminocarbonyl, (di) $C_1$–$C_6$ alkylaminocarbonyl, amino and (di) $C_1$–$C_6$ alkylamino; sulfamoyl; sulfonamido wherein the N is substituted with $C_1$–$C_6$ alkyl; $QR^6$ wherein Q is —O— or $S(O)_m$— and $R^6$ is selected from hydrogen, $C_1$–$C_6$ alkyl, $C_1$–$C_6$ haloalkyl, cyano-$C_1$–$C_6$ alkyl, $C_1$–$C_6$ alkoxycarbonyl-$C_1$–$C_6$ alkyl, $C_2$–$C_4$ alkenyl, $C_3$–$C_6$ alkynyl, hydroxycarbonyl-$C_1$–$C_6$ alkyl and aminocarbonyl-$C_1$–$C_6$ alkyl wherein the nitrogen atom may be optionally substituted with $C_1$–$C_6$ alkyl, $C_1$–$C_6$ alkoxy, $C_1$–$C_6$ alkylsulfonyl, $C_1$–$C_6$ haloalkylsulfonyl, amino or (di) $C_1$–$C_6$ alkylamino; A and X are N; or an agriculturally acceptable salt thereof.

7. A compound according to claim 6 wherein R and $R^1$ are independently hydrogen, halogen, cyano, $C_1$–$C_6$ alkyl, nitro or $C_1$–$C_6$ haloalkyl; $R^2$ is hydrogen; $R^3$ is halogen; $R^4$ is hydrogen; and $R^5$ is $C_1$–$C_6$ haloalkyl.

8. A compound according to claim 1 wherein: Z is C—$R^7$ wherein $R^7$ is hydrogen; halogen; cyano; $C_1$–$C_6$ alkyl; nitro; $C_1$–$C_6$ alkoxy; $C_1$–$C_6$ haloalkyl; $C_1$–$C_6$ alkoxy-$C_1$–$C_6$-alkyl; formyl; $C_1$–$C_6$ alkylcarbonyl; $C_1$–$C_6$ alkylcarbonyloxy; $C_1$–$C_6$ alkoxycarbonyl-$C_1$–$C_6$ alkoxy; carboxy and its salts, esters and amides thereof; tetrahydrophthalimide; amino; substituted amino wherein the substituent(s) are selected from $C_1$–$C_6$ alkyl, $C_1$–$C_6$ alkoxy, hydroxy, formyl, $C_1$–$C_6$ alkylcarbonyl, $C_1$–$C_6$ alkoxycarbonyl, $C_1$–$C_6$ alkoxycarbonyl-$C_1$–$C_6$ alkylidenecarbonyl, hydroxycarbonyl-$C_1$–$C_6$ alkylidenecarbonyl, $C_1$–$C_6$ alkylsulfonyl, $C_1$–$C_6$ haloalkylsulfonyl, aminocarbonyl, (di) $C_1$–$C_6$ alkylaminocarbonyl, amino and (di) $C_1$–$C_6$ alkylamino; sulfamoyl; sulfonamido wherein the N is substituted with $C_1$–$C_6$ alkyl; $QR^6$ wherein Q is —O— or $S(O)_m$— and $R^6$ is selected from hydrogen, $C_1$–$C_6$ alkyl, $C_1$–$C_6$ haloalkyl, cyano-$C_1$–$C_6$ alkyl, $C_1$–$C_6$ alkoxycarbonyl-$C_1$–$C_6$ alkyl, $C_2$–$C_4$ alkenyl, $C_3$–$C_6$ alkynyl, hydroxycarbonyl-$C_1$–$C_6$ alkyl and aminocarbonyl-$C_1$–$C_6$ alkyl wherein the nitrogen atom may be optionally substituted with $C_1$–$C_6$ alkyl, $C_1$–$C_6$ alkoxy, $C_1$–$C_6$ alkylsulfonyl, $C_1$–$C_6$ haloalkylsulfonyl, amino or (di) $C_1$–$C_6$ alkylamino; A is C—H or C-halogen; X is N; or an agriculturally acceptable salt thereof.

9. A compound according to claim 8 wherein, $R^3$ is hydrogen, nitro or halogen; and $R^5$ is halogen or $C_1$–$C_6$ haloalkyl.

10. A compound according to claim 8 wherein R is hydrogen, halogen or nitro; $R^1$ is hydrogen, $C_1$–$C_6$ alkoxy or $C_1$–$C_6$ alkoxycarbonyl-$C_1$–$C_6$ alkoxy; $R^2$ is hydrogen; $R^3$ is hydrogen; $R^4$ is hydrogen; $R^5$ is $C_1$–$C_6$ haloalkyl and Z is C—H or C—$R^7$ wherein $R^7$ is nitro.

11. An herbicidal composition containing (A) a compound of formula (I)

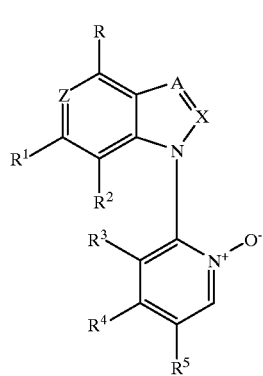

(I)

wherein:

R, $R^1$ and $R^7$ are independently hydrogen; halogen; cyano; $C_1$–$C_6$ alkyl; nitro; $C_1$–$C_6$ alkoxy; $C_1$–$C_6$ haloalkyl; $C_1$–$C_6$ alkoxy-$C_1$–$C_6$-alkyl; formyl; $C_1$–$C_6$ alkylcarbonyl; $C_1$–$C_6$ alkylcarbonyloxy; $C_1$–$C_6$ alkoxycarbonyl-$C_1$–$C_6$ alkoxy; carboxy and its salts, esters and amides thereof; tetrahydrophthalimide; amino; substituted amino wherein the substituent(s) are selected from $C_1$–$C_6$ alkyl, $C_1$–$C_6$ alkoxy, hydroxy, formyl, $C_1$–$C_6$ alkylcarbonyl, $C_1$–$C_6$ alkoxycarbonyl, $C_1$–$C_6$ alkoxycarbonyl-$C_1$–$C_6$ alkylidenecarbonyl, hydroxycarbonyl-$C_1$–$C_6$ alkylidenecarbonyl, $C_1$–$C_6$ alkylsulfonyl, $C_1$–$C_6$ haloalkylsulfonyl, aminocarbonyl, (di) $C_1$–$C_6$ alkylaminocarbonyl, amino and (di) $C_1$–$C_6$ alkylamino; sulfamoyl; sulfonamido wherein the N is substituted with $C_1$–$C_6$ alkyl; $QR^6$ wherein Q is —O— or $S(O)_m$— and $R^6$ is selected from hydrogen, $C_1$–$C_6$ alkyl, $C_1$–$C_6$ haloalkyl, cyano-$C_1$–$C_6$ alkyl, $C_1$–$C_6$ alkoxycarbonyl-$C_1$–$C_6$ alkyl, $C_2$–$C_4$ alkenyl, $C_3$–$C_6$ alkynyl, hydroxycarbonyl-$C_1$–$C_6$ alkyl and aminocarbonyl-$C_1$–$C_6$ alkyl wherein the nitrogen atom may be optionally substituted with $C_1$–$C_6$ alkyl, $C_1$–$C_6$ alkoxy, $C_1$–$C_6$ alkylsulfonyl, $C_1$–$C_6$ haloalkylsulfonyl, amino or (di) $C_1$–$C_6$ alkylamino;

$R^2$ is hydrogen, halogen, $C_1$–$C_6$ alkyl or nitro;

$R^3$ is hydrogen, nitro, halogen, cyano, $C_1$–$C_6$ alkyl-$S(O)_m$— or $C_1$–$C_6$ alkoxy;

$R^4$ is hydrogen or halogen;

$R^5$ is halogen, $C_1$–$C_6$ haloalkyl, cyano, or $C_1$–$C_6$ alkyl-$S(O)_m$—;

Z is N or C—$R^7$ wherein $R^7$ is defined as above; and

A and X are independently N, C—H or C-halogen; m is 0, 1 or 2; or an agriculturally acceptable salt thereof; and (B) a carrier therefor.

12. An herbicidal composition according to claim 11 wherein Z is N; and A and X are C—H or an agriculturally acceptable salt thereof.

13. An herbicidal composition according to claim 11 wherein R is halogen; cyano; $C_1$–$C_6$ alkyl; $C_1$–$C_6$ haloalkyl; $C_1$–$C_6$ alkoxy-$C_1$–$C_6$-alkyl; formyl; $C_1$–$C_6$ alkylcarbonyl; $C_1$–$C_6$ alkylcarbonyloxy; $C_1$–$C_6$ alkoxycarbonyl-$C_1$–$C_6$ alkoxy; carboxy and its salts, esters and amides thereof; tetrahydrophthalimide; amino; substituted amino wherein the substituent(s) are selected from $C_1$–$C_6$ alkyl, $C_1$–$C_6$ alkoxy, hydroxy, formyl, $C_1$–$C_6$ alkylcarbonyl, $C_1$–$C_6$ alkoxycarbonyl, $C_1$–$C_6$ alkoxycarbonyl-$C_1$–$C_6$ alkylidenecarbonyl, hydroxycarbonyl-$C_1$–$C_6$ alkylidenecarbonyl, $C_1$–$C_6$ alkylsulfonyl, $C_1$–$C_6$ haloalkylsulfonyl, aminocarbonyl, (di) $C_1$–$C_6$ alkylaminocarbonyl, amino and (di) $C_1$–$C_6$ alkylamino; sulfamoyl; sulfonamido wherein the N is substituted with $C_1$–$C_6$ alkyl; $QR^6$ wherein Q is —O— or $S(O)_m$— and $R^6$ is selected from hydrogen, $C_1$–$C_6$ alkyl, $C_1$–$C_6$ haloalkyl, cyano-$C_1$–$C_6$ alkyl, $C_1$–$C_6$ alkoxycarbonyl-$C_1$–$C_6$ alkyl, $C_2$–$C_4$ alkenyl, $C_3$–$C_6$ alkynyl, hydroxycarbonyl-$C_1$–$C_6$ alkyl and aminocarbonyl-$C_1$–$C_6$ alkyl wherein the nitrogen atom may be optionally substituted with $C_1$–$C_6$ alkyl, $C_1$–$C_6$ alkoxy, $C_1$–$C_6$ alkylsulfonyl, $C_1$–$C_6$ haloalkylsulfonyl, amino or (di) $C_1$–$C_6$ alkylamino; Z is N; and A and X are CH or an agriculturally acceptable salt thereof.

14. An herbicidal composition according to claim 13 wherein $R^3$ is chloro or fluoro; $R^4$ is hydrogen and $R^5$ is trifluoromethyl.

15. An herbicidal composition according to claim 13 wherein R is chloro; $R^1$ is hydrogen; $R^2$ is hydrogen; $R^3$ is hydrogen; $R^4$ is hydrogen and $R^5$ is trifluoromethyl.

16. An herbicidal composition according to claim 11 wherein Z is C—$R^7$ wherein $R^7$ is hydrogen; halogen; cyano; $C_1$–$C_6$ alkyl; nitro; $C_1$–$C_6$ alkoxy; $C_1$–$C_6$ haloalkyl; $C_1$–$C_6$ alkoxy-$C_1$–$C_6$-alkyl; formyl; $C_1$–$C_6$ alkylcarbonyl; $C_1$–$C_6$ alkylcarbonyloxy; $C_1$–$C_6$ alkoxycarbonyl-$C_1$–$C_6$ alkoxy; carboxy and its salts, esters and amides thereof; tetrahydrophthalimide; amino; substituted amino wherein the substituent(s) are selected from $C_1$–$C_6$ alkyl, $C_1$–$C_6$ alkoxy, hydroxy, formyl, $C_1$–$C_6$ alkylcarbonyl, $C_1$–$C_6$ alkoxycarbonyl, $C_1$–$C_6$ alkoxycarbonyl-$C_1$–$C_6$ alkylidenecarbonyl, hydroxycarbonyl-$C_1$–$C_6$ alkylidenecarbonyl, $C_1$–$C_6$ alkylsulfonyl, $C_1$–$C_6$ haloalkylsulfonyl, aminocarbonyl, (di) $C_1$–$C_6$ alkylaminocarbonyl, amino and (di) $C_1$–$C_6$ alkylamino; sulfamoyl; sulfonamido wherein the N is substituted with $C_1$–$C_6$ alkyl; $QR^6$ wherein Q is —O— or $S(O)_m$— and $R^6$ is selected from hydrogen, $C_1$–$C_6$ alkyl, $C_1$–$C_6$ haloalkyl, cyano-$C_1$–$C_6$ alkyl, $C_1$–$C_6$ alkoxycarbonyl-$C_1$–$C_6$ alkyl, $C_2$–$C_4$ alkenyl, $C_3$–$C_6$ alkynyl, hydroxycarbonyl-$C_1$–$C_6$ alkyl and aminocarbonyl-$C_1$–$C_6$ alkyl wherein the nitrogen atom may be optionally substituted with $C_1$–$C_6$ alkyl, $C_1$–$C_6$ alkoxy, $C_1$–$C_6$ alkylsulfonyl, $C_1$–$C_6$ haloalkylsulfonyl, amino or (di) $C_1$–$C_6$ alkylamino; A and X are N; or an agriculturally acceptable salt thereof.

17. An herbicidal compostion according to claim 16 wherein R and $R^1$ are independently hydrogen, halogen, cyano, $C_1$–$C_6$ alkyl, nitro or $C_1$–$C_6$ haloalkyl; $R^2$ is hydrogen; $R^3$ is halogen; $R^4$ is hydrogen; and $R^5$ is $C_1$–$C_6$ haloalkyl.

18. A herbicidal composition according to claim 11 wherein: Z is C—$R^7$ wherein $R^7$ is hydrogen; halogen; cyano; $C_1$–$C_6$ alkyl; nitro; $C_1$–$C_6$ alkoxy; $C_1$–$C_6$ haloalkyl; $C_1$–$C_6$ alkoxy-$C_1$–$C_6$-alkyl; formyl; $C_1$–$C_6$ alkylcarbonyl; $C_1$–$C_6$ alkylcarbonyloxy; $C_1$–$C_6$ alkoxycarbonyl-$C_1$–$C_6$ alkoxy; carboxy and its salts, esters and amides thereof; tetrahydrophthalimide; amino; substituted amino wherein the substituent(s) are selected from $C_1$–$C_6$ alkyl, $C_1$–$C_6$ alkoxy, hydroxy, formyl, $C_1$–$C_6$ alkylcarbonyl, $C_1$–$C_6$ alkoxycarbonyl, $C_1$–$C_6$ alkoxycarbonyl-$C_1$–$C_6$ alkylidenecarbonyl, hydroxycarbonyl-$C_1$–$C_6$ alkylidenecarbonyl, $C_1$–$C_6$ alkylsulfonyl, $C_1$–$C_6$ haloalkylsulfonyl, aminocarbonyl, (di) $C_1$–$C_6$ alkylaminocarbonyl, amino and (di) $C_1$–$C_6$ alkylamino; sulfamoyl; sulfonamido wherein the N is substituted with $C_1$–$C_6$ alkyl; $QR^6$ wherein Q is —O— or $S(O)_m$— and $R^6$ is selected from hydrogen, $C_1$–$C_6$ alkyl, $C_1$–$C_6$ haloalkyl, cyano-$C_1$–$C_6$ alkyl, $C_1$–$C_6$ alkoxycarbonyl-$C_1$–$C_6$ alkyl, $C_2$–$C_4$ alkenyl, $C_3$–$C_6$ alkynyl, hydroxycarbonyl-$C_1$–$C_6$ alkyl and aminocarbonyl-$C_1$–$C_6$ alkyl wherein the nitrogen atom may be optionally substituted with $C_1$–$C_6$ alkyl, $C_1$–$C_6$ alkoxy, $C_1$–$C_6$ alkylsulfonyl, $C_1$–$C_6$ haloalkylsulfonyl, amino or (di) $C_1$–$C_6$ alkylamino; A is C—H or C-halogen; X is N; or an agriculturally acceptable salt thereof.

19. An herbicidal composition according to claim 18 wherein $R^3$ is hydrogen, nitro or halogen; and $R^5$ is halogen or $C_1$–$C_6$ haloalkyl.

20. An herbicidal compostion according to claim 18 wherein R is hydrogen, halogen or nitro; $R^1$ is hydrogen, $C_1$–$C_6$ alkoxy or $C_1$–$C_6$ alkoxycarbonyl-$C_1$–$C_6$ alkoxy; $R^2$ is hydrogen; $R^3$ is hydrogen; $R^4$ is hydrogen; $R^5$ is $C_1$–$C_6$ haloalkyl and Z is C—H or C—$R^7$ wherein $R^7$ is nitro.

21. A method for controlling undesirable vegetation by applying to an area where such vegetation control is desired an herbicidally effective amount of a compound of formula (I):

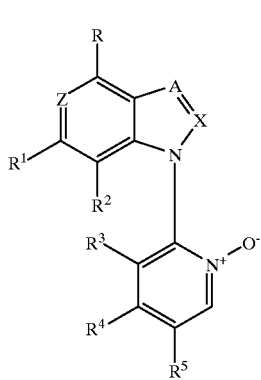

wherein: R, $R^1$ and $R^7$ are independently hydrogen; halogen; cyano; $C_1$–$C_6$ alkyl; nitro; $C_1$–$C_6$ alkoxy; $C_1$–$C_6$ haloalkyl; $C_1$–$C_6$ alkoxy-$C_1$–$C_6$-alkyl; formyl; $C_1$–$C_6$ alkylcarbonyl; $C_1$–$C_6$ alkylcarbonyloxy; $C_1$–$C_6$ alkoxycarbonyl-$C_1$–$C_6$ alkoxy; carboxy and its salts, esters and amides thereof; tetrahydrophthalimide; amino; substituted amino wherein the substituent(s) are selected from $C_1$–$C_6$ alkyl, $C_1$–$C_6$ alkoxy, hydroxy, formyl, $C_1$–$C_6$ alkylcarbonyl, $C_1$–$C_6$ alkoxycarbonyl, $C_1$–$C_6$ alkoxycarbonyl-$C_1$–$C_6$ alkylidenecarbonyl, hydroxycarbonyl-$C_1$–$C_6$ alkylidenecarbonyl, $C_1$–$C_6$ alkylsulfonyl, $C_1$–$C_6$ haloalkylsulfonyl, aminocarbonyl, (di) $C_1$–$C_6$ alkylaminocarbonyl, amino and (di) $C_1$–$C_6$ alkylamino; sulfamoyl; sulfonamido wherein the N is substituted with $C_1$–$C_6$ alkyl; $QR^6$ wherein Q is —O— or $S(O)_m$— and $R^6$ is selected from hydrogen, $C_1$–$C_6$ alkyl, $C_1$–$C_6$ haloalkyl, cyano-$C_1$–$C_6$ alkyl, $C_1$–$C_6$ alkoxycarbonyl-$C_1$–$C_6$ alkyl, $C_2$–$C_4$ alkenyl, $C_3$–$C_6$ alkynyl, hydroxycarbonyl-$C_1$–$C_6$ alkyl and aminocarbonyl-$C_1$–$C_6$ alkyl wherein the nitrogen atom may be optionally substituted with $C_1$–$C_6$ alkyl, $C_1$–$C_6$ alkoxy, $C_1$–$C_6$ alkylsulfonyl, $C_1$–$C_6$ haloalkylsulfonyl, amino or (di) $C_1$–$C_6$ alkylamino;

$R^2$ is hydrogen, halogen, $C_1$–$C_6$ alkyl or nitro;

$R^3$ is hydrogen, nitro, halogen, cyano, $C_1$–$C_6$ alkyl-$S(O)_m$— or $C_1$–$C_6$ alkoxy;

$R^4$ is hydrogen or halogen;

$R^5$ is halogen, $C_1$–$C_6$ haloalkyl, cyano, or $C_1$–$C_6$ alkyl-$S(O)_m$—;

Z is N or C—$R^7$ wherein $R^7$ is defined as above; and

A and X are independently N, C—H or C-halogen; m is 0, 1 or 2; or an agriculturally acceptable salt thereof.

22. A method according to claim 21 wherein Z is N; and A and X are C—H or an agriculturally acceptable salt thereof.

23. A method according to claim 21 wherein R is halogen; cyano; $C_1$–$C_6$ alkyl; $C_1$–$C_6$ haloalkyl; $C_1$–$C_6$ alkoxy-$C_1$–$C_6$-alkyl; formyl; $C_1$–$C_6$ alkylcarbonyl; $C_1$–$C_6$ alkylcarbonyloxy; $C_1$–$C_6$ alkoxycarbonyl-$C_1$–$C_6$ alkoxy; carboxy and its salts, esters and amides thereof; tetrahydrophthalimide; amino; substituted amino wherein the substituent(s) are selected from $C_1$–$C_6$ alkyl, $C_1$–$C_6$ alkoxy, hydroxy, formyl, $C_1$–$C_6$ alkylcarbonyl, $C_1$–$C_6$ alkoxycarbonyl, $C_1$–$C_6$ alkoxycarbonyl-$C_1$–$C_6$ alkylidenecarbonyl, hydroxycarbonyl-$C_1$–$C_6$ alkylidenecarbonyl, $C_1$–$C_6$ alkylsulfonyl, $C_1$–$C_6$ haloalkylsulfonyl, aminocarbonyl, (di) $C_1$–$C_6$ alkylaminocarbonyl, amino and (di) $C_1$–$C_6$ alkylamino; sulfamoyl; sulfonamido wherein the N is substituted with $C_1$–$C_6$ alkyl; $QR^6$ wherein Q is —O— or $S(O)_m$— and $R^6$ is selected from hydrogen, $C_1$–$C_6$ alkyl, $C_1$–$C_6$ haloalkyl, cyano-$C_1$–$C_6$ alkyl, $C_1$–$C_6$ alkoxycarbonyl-$C_1$–$C_6$ alkyl, $C_2$–$C_4$ alkenyl, $C_3$–$C_6$ alkynyl, hydroxycarbonyl-$C_1$–$C_6$ alkyl and aminocarbonyl-$C_1$–$C_6$ alkyl wherein the nitrogen atom may be optionally substituted with $C_1$–$C_6$ alkyl, $C_1$–$C_6$ alkoxy, $C_1$–$C_6$ alkylsulfonyl, $C_1$–$C_6$ haloalkylsulfonyl, amino or (di) $C_1$–$C_6$ alkylamino; Z is N; and A and X are CH or an agriculturally acceptable salt thereof.

24. A method according to claim 23 wherein $R^3$ is chloro or fluoro; $R^4$ is hydrogen and $R^5$ is trifluoromethyl.

25. A method according to claim 23 wherein R is chloro; $R^1$ is hydrogen; $R^2$ is hydrogen; $R^3$ is hydrogen; $R^4$ is hydrogen and $R^5$ is trifluoromethyl.

26. A method according to claim 21 wherein Z is C—$R^7$ wherein $R^7$ is hydrogen; halogen; cyano; $C_1$–$C_6$ alkyl; nitro; $C_1$–$C_6$ alkoxy; $C_1$–$C_6$ haloalkyl; $C_1$–$C_6$ alkoxy-$C_1$–$C_6$-alkyl; formyl; $C_1$–$C_6$ alkylcarbonyl; $C_1$–$C_6$ alkylcarbonyloxy; $C_1$–$C_6$ alkoxycarbonyl-$C_1$–$C_6$ alkoxy; carboxy and its salts, esters and amides thereof; tetrahydrophthalimide; amino; substituted amino wherein the substituent(s) are selected from $C_1$–$C_6$ alkyl, $C_1$–$C_6$ alkoxy, hydroxy, formyl, $C_1$–$C_6$ alkylcarbonyl, $C_1$–$C_6$ alkoxycarbonyl, $C_1$–$C_6$ alkoxycarbonyl-$C_1$–$C_6$ alkylidenecarbonyl, hydroxycarbonyl-$C_1$–$C_6$ alkylidenecarbonyl, $C_1$–$C_6$ alkylsulfonyl, $C_1$–$C_6$ haloalkylsulfonyl, aminocarbonyl, (di) $C_1$–$C_6$ alkylaminocarbonyl, amino and (di) $C_1$–$C_6$ alkylamino; sulfamoyl; sulfonamido wherein the N is substituted with $C_1$–$C_6$ alkyl; $QR^6$ wherein Q is —O— or $S(O)_m$— and $R^6$ is selected from hydrogen, $C_1$–$C_6$ alkyl, $C_1$–$C_6$ haloalkyl, cyano-$C_1$–$C_6$ alkyl, $C_1$–$C_6$ alkoxycarbonyl-$C_1$–$C_6$ alkyl, $C_2$–$C_4$ alkenyl, $C_3$–$C_6$ alkynyl, hydroxycarbonyl-$C_1$–$C_6$ alkyl and aminocarbonyl-$C_1$–$C_6$ alkyl wherein the nitrogen atom may be optionally substituted with $C_1$–$C_6$ alkyl, $C_1$–$C_6$ alkoxy, $C_1$–$C_6$ alkylsulfonyl, $C_1$–$C_6$ haloalkylsulfonyl, amino or (di) $C_1$–$C_6$ alkylamino; A and X are N; or an agriculturally acceptable salt thereof.

27. A method according to claim 26 wherein R and $R^1$ are independently hydrogen, halogen, cyano, $C_1$–$C_6$ alkyl, nitro or $C_1$–$C_6$ haloalkyl; $R^2$ is hydrogen; $R^3$ is halogen; $R^4$ is hydrogen; and $R^5$ is $C_1$–$C_6$ haloalkyl.

28. A method according to claim 21 wherein: Z is C—$R^7$ wherein $R^7$ is hydrogen; halogen; cyano; $C_1$–$C_6$ alkyl; nitro; $C_1$–$C_6$ alkoxy; $C_1$–$C_6$ haloalkyl; $C_1$–$C_6$ alkoxy-$C_1$–$C_6$-alkyl; formyl; $C_1$–$C_6$ alkylcarbonyl; $C_1$–$C_6$ alkylcarbonyloxy; $C_1$–$C_6$ alkoxycarbonyl-$C_1$–$C_6$ alkoxy; carboxy and its salts, esters and amides thereof; tetrahydrophthalimide; amino; substituted amino wherein the substituent(s) are selected from $C_1$–$C_6$ alkyl, $C_1$–$C_6$ alkoxy, hydroxy, formyl, $C_1$–$C_6$ alkylcarbonyl, $C_1$–$C_6$ alkoxycarbonyl, $C_1$–$C_6$ alkoxycarbonyl-$C_1$–$C_6$ alkylidenecarbonyl, hydroxycarbonyl-$C_1$–$C_6$ alkylidenecarbonyl, $C_1$–$C_6$ alkylsulfonyl, $C_1$–$C_6$ haloalkylsulfonyl, aminocarbonyl, (di) $C_1$–$C_6$ alkylaminocarbonyl, amino and (di) $C_1$–$C_6$ alkylamino; sulfamoyl; sulfonamido wherein the N is substituted with $C_1$–$C_6$ alkyl; $QR^6$ wherein Q is —O— or $S(O)_m$— and $R^6$ is selected from hydrogen, $C_1$–$C_6$ alkyl, $C_1$–$C_6$ haloalkyl, cyano-$C_1$–$C_6$ alkyl, $C_1$–$C_6$ alkoxycarbonyl-$C_1$–$C_6$ alkyl, $C_2$–$C_4$ alkenyl, $C_3$–$C_6$ alkynyl, hydroxycarbonyl-$C_1$–$C_6$ alkyl and aminocarbonyl-$C_1$–$C_6$ alkyl wherein the nitrogen atom may be optionally substituted with $C_1$–$C_6$ alkyl, $C_1$–$C_6$ alkoxy, $C_1$–$C_6$ alkylsulfonyl, $C_1$–$C_6$ haloalkylsulfonyl, amino or (di) $C_1$–$C_6$ alkylamino; A is C—H or C-halogen; X is N; or an agriculturally acceptable salt thereof.

29. A method according to claim 28 wherein, $R^3$ is hydrogen, nitro or halogen; and $R^5$ is halogen or $C_1$–$C_6$ haloalkyl.

30. A method according to claim 28 wherein R is hydrogen, halogen or nitro; $R^1$ is hydrogen, $C_1$–$C_6$ alkoxy or $C_1$–$C_6$ alkoxycarbonyl-$C_1$–$C_6$ alkoxy; $R^2$ is hydrogen; $R^3$ is hydrogen; $R^4$ is hydrogen; $R^5$ is $C_1$–$C_6$ haloalkyl and Z is C—H or C—$R^7$ wherein $R^7$ is nitro.

* * * * *